US008535236B2

(12) United States Patent
Heinz et al.

(10) Patent No.: US 8,535,236 B2
(45) Date of Patent: Sep. 17, 2013

(54) APPARATUS AND METHOD FOR ANALYZING A SOUND SIGNAL USING A PHYSIOLOGICAL EAR MODEL

(75) Inventors: Thorsten Heinz, Arnstadt (DE); Andreas Brueckmann, Hessisch Lichtenau (DE); Juergen Herre, Buckenhof (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 2669 days.

(21) Appl. No.: 10/804,992

(22) Filed: Mar. 19, 2004

(65) Prior Publication Data

US 2005/0234366 A1 Oct. 20, 2005

(51) Int. Cl.
*A61B 5/00* (2006.01)

(52) U.S. Cl.
USPC ............... 600/559; 381/58; 381/60; 381/312; 381/320; 381/321; 434/112; 434/116; 434/262; 434/266; 434/267; 600/25; 607/55; 607/56; 704/200.1; 704/207; 704/216; 704/217

(58) Field of Classification Search
USPC ......... 434/262, 112, 116, 266, 267; 600/559, 600/25; 381/58, 60, 312, 320, 321; 704/207, 704/200.1, 216, 217; 607/55, 56
See application file for complete search history.

(56) References Cited

U.S. PATENT DOCUMENTS 3,441,717 A * 4/1969 Holzman et al. ................ 377/52
3,441,850 A * 4/1969 Frazer et al. ............... 324/76.26
4,366,349 A * 12/1982 Adelman ...................... 381/316
4,419,544 A * 12/1983 Adelman ...................... 381/94.3
4,905,285 A * 2/1990 Allen et al. ................... 704/232
4,980,918 A * 12/1990 Bahl et al. ...................... 704/240
5,176,620 A * 1/1993 Gilman ........................... 600/25
5,381,512 A * 1/1995 Holton et al. .............. 704/200.1
5,388,182 A * 2/1995 Benedetto et al. ............ 704/205
5,417,113 A * 5/1995 Hartley ........................... 73/587
5,473,759 A * 12/1995 Slaney et al. ................. 704/266
5,664,577 A * 9/1997 Lonsbury-Martin et al. . 600/559

(Continued)

OTHER PUBLICATIONS

Ray Meddis and Michael J. Hewitt, "Virtual pitch and phase sensitivity of a computer model of the auditory periphery. I: Pitch identification", Jan. 24, 1991, Acoustical Societ of America, pp. 2866-2882.*

(Continued)

*Primary Examiner* — Jack Yip
(74) *Attorney, Agent, or Firm* — Michael A. Glenn; Perkins Coie LLP

(57) ABSTRACT

An apparatus for analyzing a sound signal is based on an ear model for deriving, for a number of inner hair cells, an estimate for a time-varying concentration of transmitter substance inside a cleft between an inner hair cell and an associated auditory nerve from the sound signal so that an estimated inner hair cell cleft contents map over time is obtained. This map is analyzed by means of a pitch analyzer to obtain a pitch line over time, the pitch line indicating a pitch of the sound signal for respective time instants. A rhythm analyzer is operative for analyzing envelopes of estimates for selected inner hair cells, the inner hair cells being selected in accordance with the pitch line, so that segmentation instants are obtained, wherein a segmentation instant indicates an end of the preceding note or a start of a succeeding note. Thus, a human-related and reliable sound signal analysis can be obtained.

28 Claims, 10 Drawing Sheets

Peter and the wolf: Score

(56) References Cited

U.S. PATENT DOCUMENTS

| | | | | |
|---|---|---|---|---|
| 5,776,179 | A * | 7/1998 | Ren et al. | 607/137 |
| 5,918,223 | A * | 6/1999 | Blum et al. | 1/1 |
| 6,476,308 | B1 * | 11/2002 | Zhang | 84/616 |
| 6,525,255 | B1 * | 2/2003 | Funaki | 84/616 |
| 6,542,869 | B1 * | 4/2003 | Foote | 704/500 |
| 6,719,707 | B1 * | 4/2004 | Montgomery | 600/586 |
| 6,862,558 | B2 * | 3/2005 | Huang | 702/194 |
| 7,012,183 | B2 * | 3/2006 | Herre et al. | 84/611 |
| 7,068,723 | B2 * | 6/2006 | Foote et al. | 375/240.25 |
| 7,076,308 | B1 * | 7/2006 | Overstreet et al. | 607/57 |
| 7,574,265 | B1 * | 8/2009 | Overstreet et al. | 607/57 |
| 7,602,985 | B2 * | 10/2009 | Gao et al. | 382/240 |
| 7,616,771 | B2 * | 11/2009 | Lenhardt et al. | 381/326 |
| 2003/0033094 | A1 * | 2/2003 | Huang | 702/39 |
| 2003/0171786 | A1 * | 9/2003 | Blamey et al. | 607/57 |
| 2004/0068401 | A1 * | 4/2004 | Herre et al. | 704/217 |
| 2004/0094019 | A1 * | 5/2004 | Herre et al. | 84/611 |
| 2006/0188115 | A1 * | 8/2006 | Lenhardt et al. | 381/312 |
| 2007/0005348 | A1 * | 1/2007 | Klefenz | 704/202 |
| 2008/0049948 | A1 * | 2/2008 | Christoph et al. | 381/86 |
| 2008/0181422 | A1 * | 7/2008 | Christoph | 381/73.1 |
| 2008/0285775 | A1 * | 11/2008 | Christoph et al. | 381/99 |
| 2009/0222228 | A1 * | 9/2009 | Gao et al. | 702/67 |

OTHER PUBLICATIONS

Ray Meddis, "Simulation of mechanical to neural transduction in the auditory receptor", Oct. 16, 1985, Acoustical Societ of America, pp. 702-711.*

L. P. Clarisse, J. P. Martens, M. Lesaffre, B. De Baets, H. De Meyer and M. Leman, "An Auditory Model Based Transcriber of Singing Sequences", 2002, IRCAM—Centre Pompidou, pp. 1-8.*

Christian J. Sumnera, Enrique A. Lopez-Poveda, Lowel P. O'Mard and Ray Meddis, "Adaptation in a revised inner-hair cell model", Aug. 30, 2002, Acoustical Society of America, pp. 893-901.*

Dubnov et al., "Timbre Recognition with Combined Stationary and Temporal Features", 1998, Proceeding of International Computer Music Conference, pp. 1-9.*

Heinz and Bruckmann, "Using a Physiological Ear Model for Automatic Melody Transcription and Sound Source Recognition", Audio Engineering Society Convention Paper, Mar. 2003, Amsterdam, The Netherlands.

* cited by examiner

FIG 1 Peter and the wolf: Score
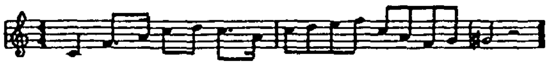
FIG 2 Peter and the wolf: Sound wave
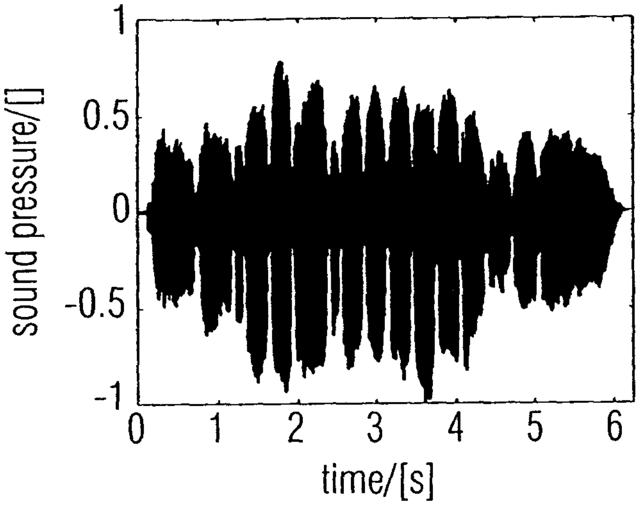
FIG 3 IHC cleft contents
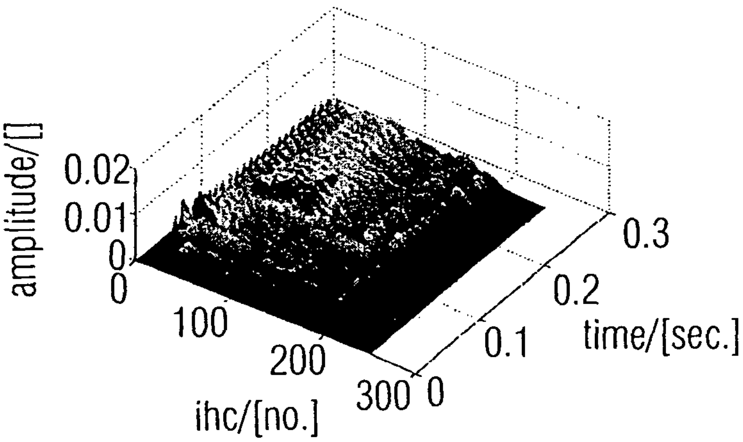

FIG 4. Cleft content of IHC #12
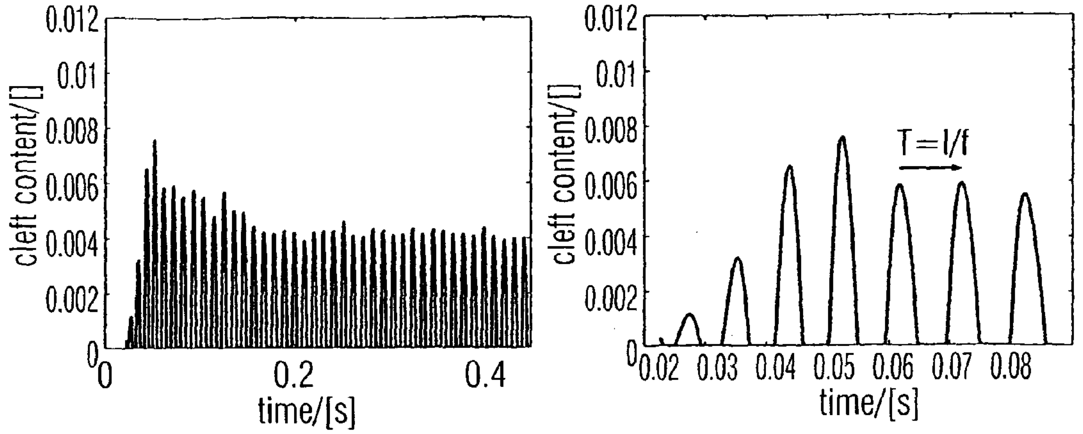
FIG 5. Cleft content of IHC #12
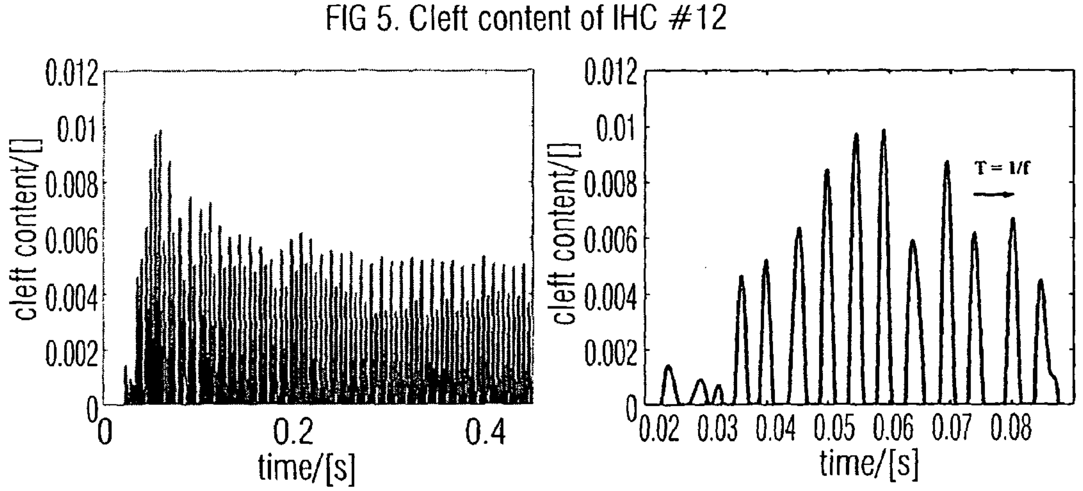
FIG 6. SACF histogram
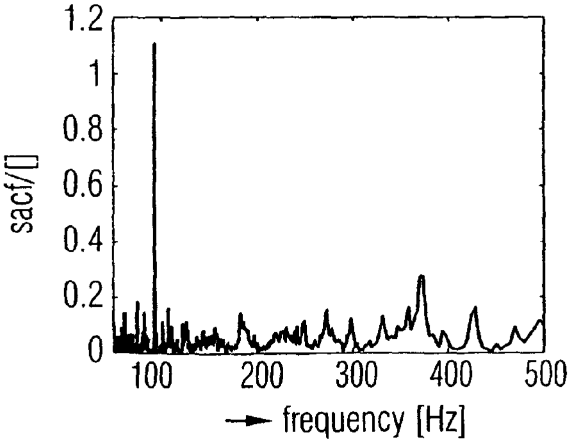

FIG 7: Initial pitch estimation vs. cleaned pitch trajectories
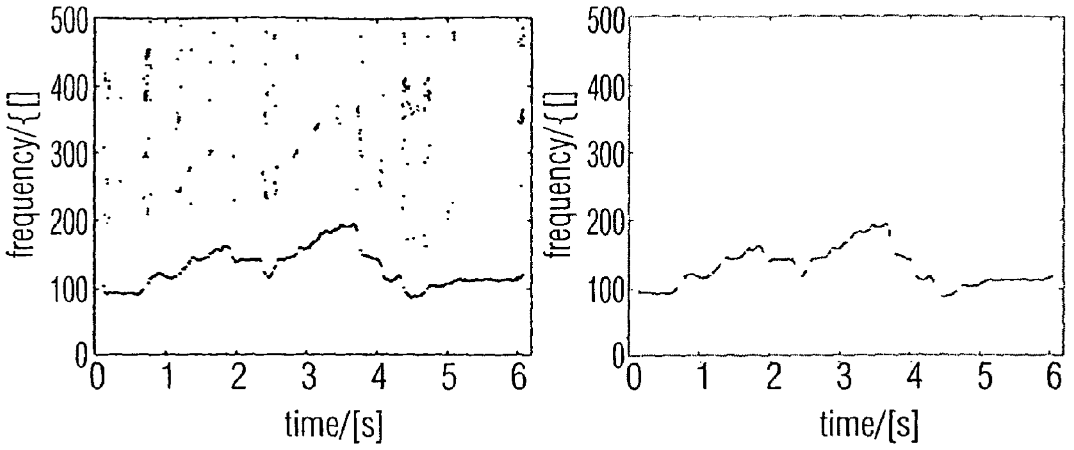
FIG 8: Envelopes of transmitter substance: 1st and 4th partial
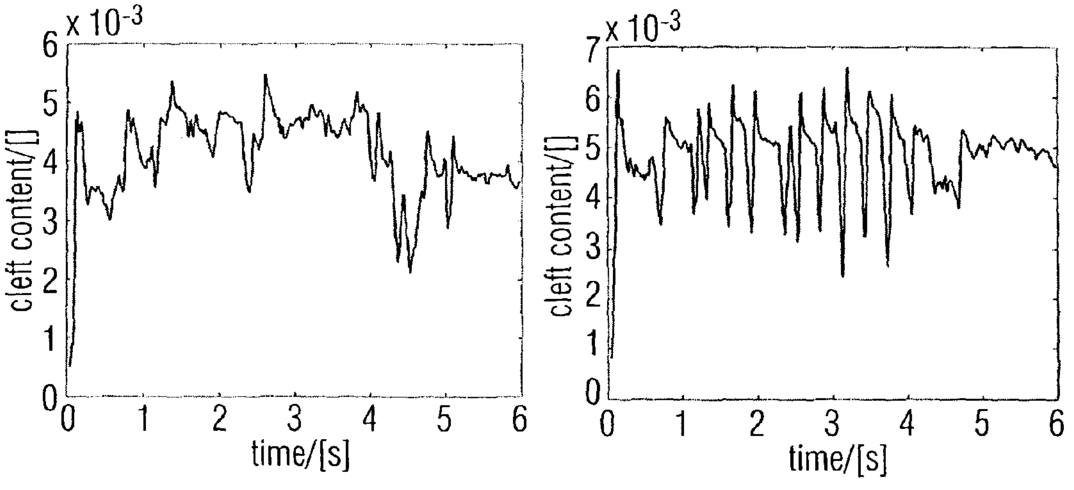

FIG 9: Onset map
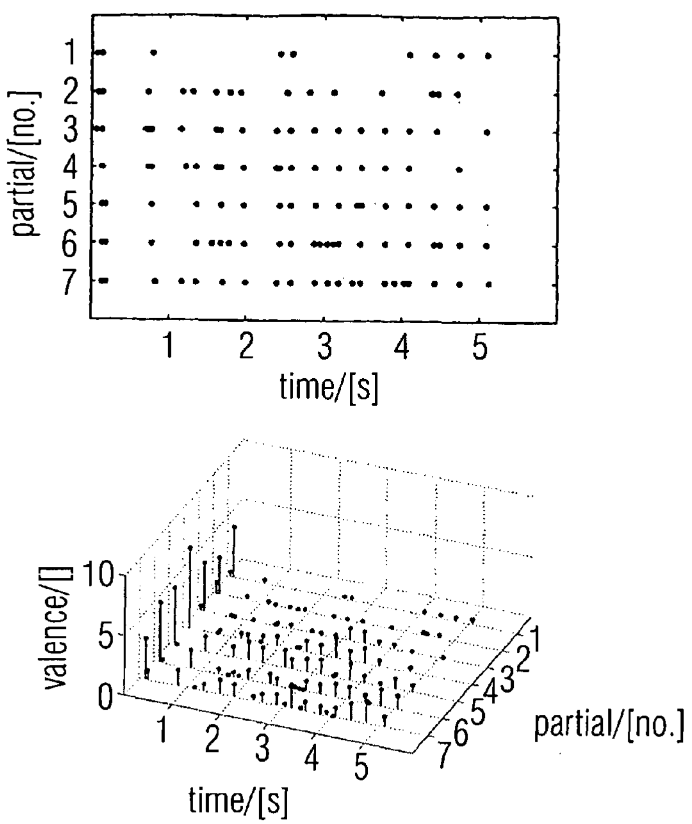
FIG 10: Onset masking
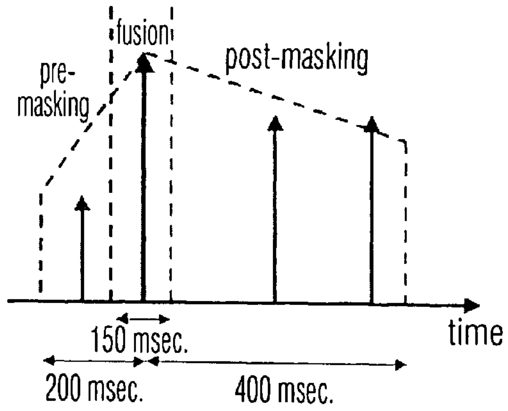
FIG 11: Onset histogram
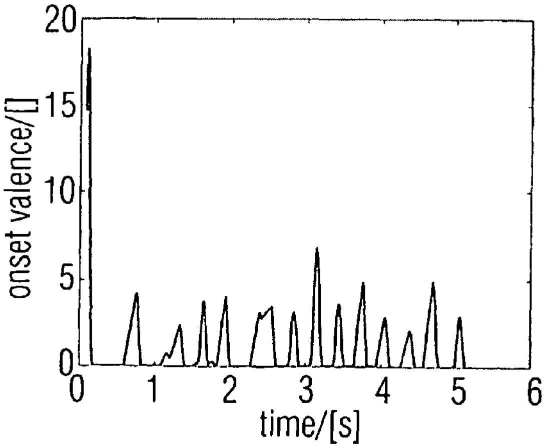

FIG 12: Pitch trajectories, segmented

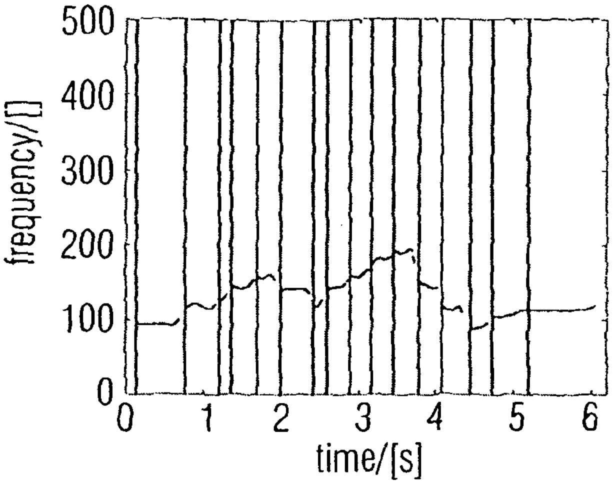

FIG 13: Feature values, clarinet Bb3

| partial [no.] | onset time [s] | frequency [Hz] | amplitude [] | IHC peak [no.] | IHC resonance [no.] |
|---|---|---|---|---|---|
| 1 | 0.187 | 236.4 | 0.00878 | 27 | 30 |
| 2 | 0.218 | 467.8 | 0.00555 | 48 | 14 |
| 3 | 0.192 | 703.5 | 0.00862 | 73 | 36 |
| 4 | 0.219 | 878.2 | 0.00735 | 94 | 2 |
| 5 | 0.201 | 1170.6 | 0.00733 | 102 | 12 |
| 6 | 0.202 | 1405.3 | 0.00776 | 113 | 12 |
| 7 | 0.206 | 1640.8 | 0.00783 | 123 | 16 |

FIG 14: Query-By-Humming: 1152 query inputs

| | | EarAnalyzer | Extreme | Hough |
|---|---|---|---|---|
| database 1 (200 pieces) | Position 1 | 82.8 % | 59.5 % | 39.9 % |
| | Top 10 | 92.5 % | 75.1 % | 56.9 % |
| database 2 (1024 pieces) | Position 1 | 78.5 % | 53.5 % | 32.0 % |
| | Top 10 | 88.9 % | 67.9 % | 42.9 % |

FIG 15: Query-By-Humming incl. GSM distortion: 1152 query inputs

| | | EarAnalyzer | Extreme | Hough |
|---|---|---|---|---|
| Fullrate | Position 1 | 79.3 % | 49.4 % | 42.0 % |
| | Top 10 | 88.9 % | 67.1 % | 56.3 % |
| Enhanced Fullrate | Position 1 | 80.6 % | 60.4 % | 45.0 % |
| | Top 10 | 91.2 % | 73.9 % | 62.7 % |
| Halfrate | Position 1 | 69.9 % | 48.4 % | 30.2 % |
| | Top 10 | 82.5 % | 65.4 % | 49.0 % |
| Original | Position 1 | 82.8 % | 59.5 % | 39.9 % |
| | Top 10 | 92.5 % | 75.1 % | 56.9 % |

FIG 16: Instrument recognition rates [total (clarinet|oboe|bassoon)]
| training vs. query | McGill [%] | Gdansk [%] | Fraunhofer [%] |
|---|---|---|---|
| McGill | 100 (100\|100\|100) | 80 ( 94\| 47\| 94) | 88 ( 97\| 67\| 97) |
| Gdansk | 85 ( 75\| 87\| 94) | 100 (100\|100\|100) | 87 ( 86\| 73\|100) |
| Fraunhofer | 81 ( 58\| 93\| 94) | 72 ( 64\| 60\| 94) | 100 (100\|100\|100) |
| McGill + Gdansk | 99 ( 97\|100\|100) | 100 (100\|100\|100) | 91 ( 92\| 83\| 97) |
| McGill + Fraunhofer | 100 (100\|100\|100) | 83 ( 92\| 53\|100) | 100 (100\|100\|100) |
| Gdansk + Fraunhofer | 88 ( 78\| 93\| 94) | 100 (100\|100\|100) | 100 (100\|100\|100) |
FIG 17: extended analog model by Baumgarte
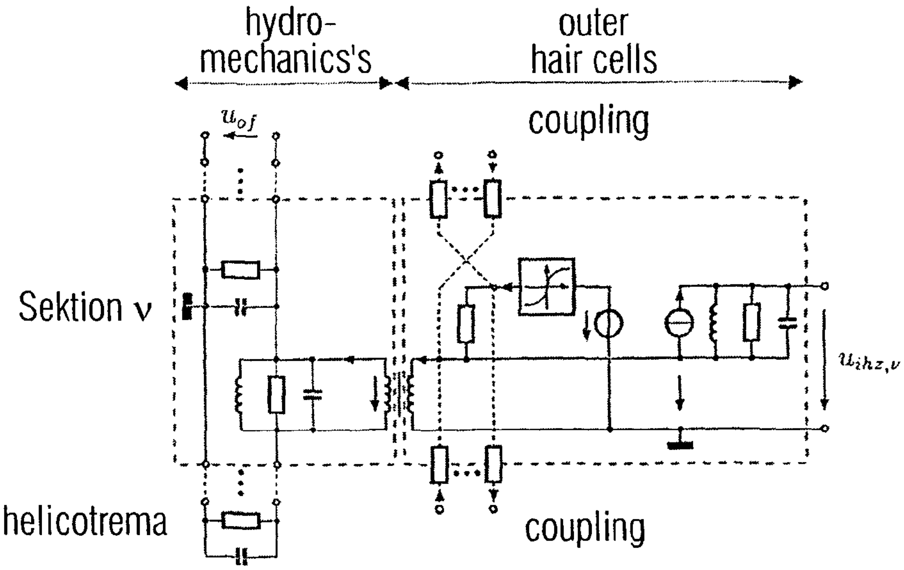
FIG 18: hair cell model by Meddis
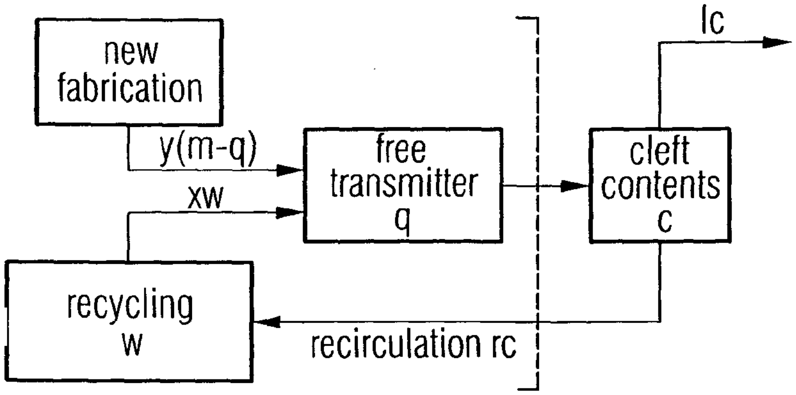

FIG 19: mathematical description of the model in Fig 18
$$k = \begin{cases} gdt \cdot \left(\frac{s+A}{s+A+B}\right) & : \quad s+A \geq 0 \\ 0 & : \quad s+A < 0. \end{cases}$$
$$\frac{dq}{dt} = y(m-q) + xw - kq,$$
$$\frac{dc}{dt} = kq - lc - rc,$$
$$\frac{dw}{dt} = rc - xw.$$
| | | |
|---|---|---|
| A | = | 10 |
| B | = | 3000 |
| x | = | 66.31 |
| g | = | 1000 |
| y | = | 5.05 |
| m | = | 1 |
| l | = | 2500 |
| r | = | 6580 |
FIG 20: crossection of the cochlea
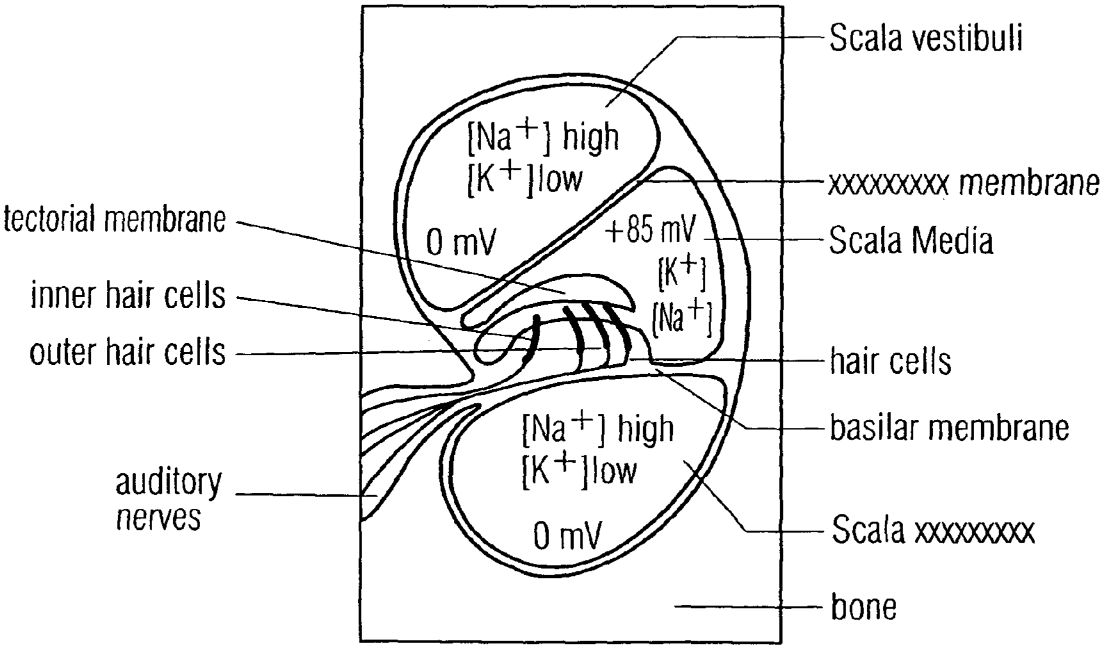

FIG 22 (pitch analyzer)
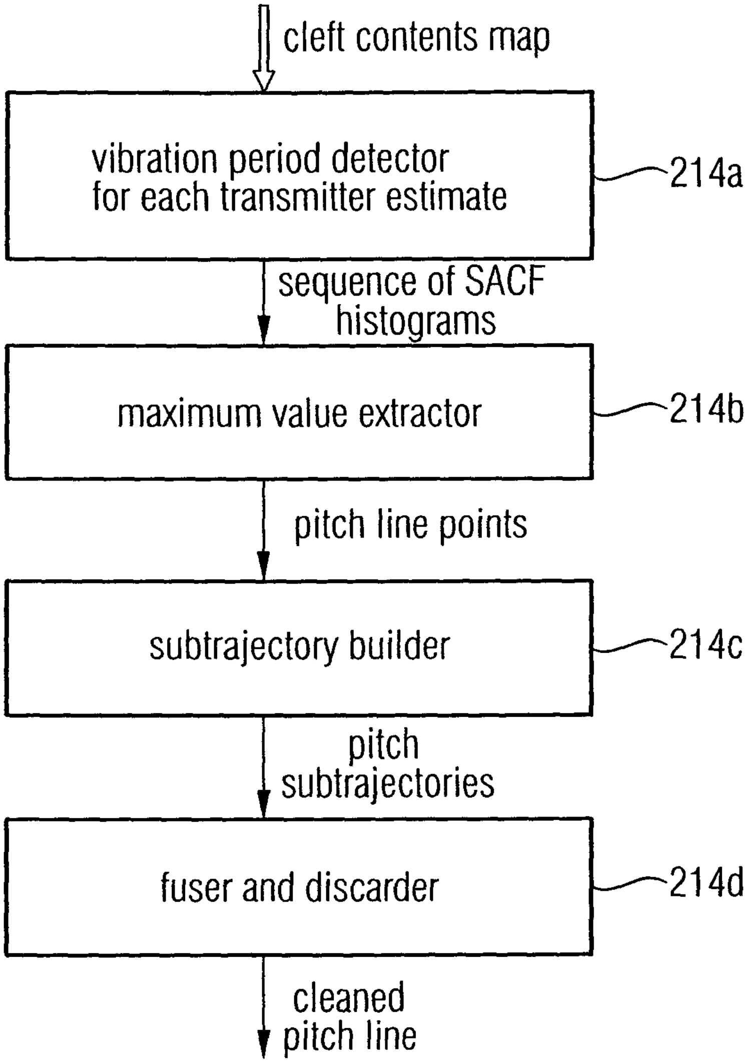

FIG 23 (rhythm analyzer)
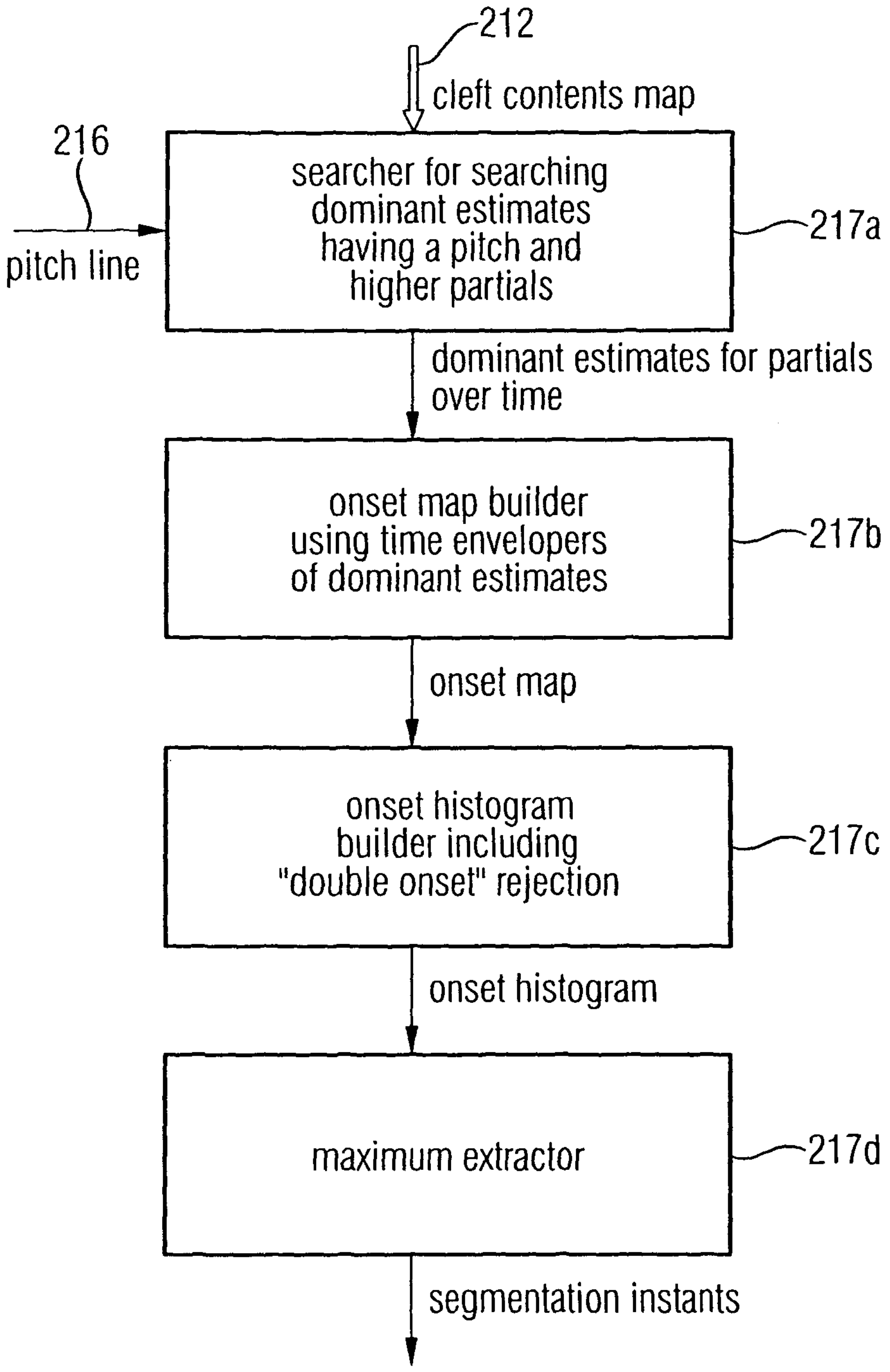

APPARATUS AND METHOD FOR ANALYZING A SOUND SIGNAL USING A PHYSIOLOGICAL EAR MODEL

FIELD OF THE INVENTION

The present invention relates to sound analysis tools and, in particular, to an apparatus and a method for analyzing a sound signal for the purpose of, for example, a sound transcription or timbre recognition.

BACKGROUND OF THE INVENTION AND PRIOR ART

Concepts by means of which time signals having a harmonic portion, such as audio data, are identifiable and able to be referenced are useful for many users. Especially in a situation where there is an audio signal whose title and author are unknown, it is often desirable to find out who the respective song originates from. A need for this exists, for example, if there is a desire to acquire, e.g., a CD of the performer in question. If the present audio signal includes only the time-signal content but no name concerning the performer, the music publishers, etc., no identification of the origin of the audio signal or of the person or institution a song originates from will be possible. The only hope then has been to hear the audio piece once again, including reference data with regard to the author or the source where the audio signal is to be purchased, so as to be able to procure the song desired.

It is not possible to search audio data using conventional search machines on the Internet since the search engine know only how to deal with textual data. Audio signals, or, more generally speaking, time signals having a harmonic portion may not be processed by such search engines unless they include textual search indications.

A realistic stock of audio files comprises several thousand stored audio files up to hundred thousands of audio files. Music database information may be stored on a central Internet server, and potential search enquiries may be effected via the Internet. Alternatively, with today's hard disc capacities, it would also be feasible to have these central music databases on users' local hard disc systems. It is desirable to be able to browse such music databases to obtain reference data about an audio file of which only the file itself but no reference data is known.

In addition, it is equally desirable to be able to browse music databases using specified criteria, for example such as to be able to find out similar pieces. Similar pieces are, for example, such pieces which have a similar tune, a similar set of instruments or simply similar sounds, such as, for example, the sound of the sea, bird sounds, male voices, female voices, etc.

The U.S. Pat. No. 5,918,223 discloses a method and an apparatus for a content-based analysis, storage, retrieval and segmentation of audio information. This method is based on extracting several acoustic features from an audio signal. What is measured are volume, bass, pitch, brightness, and Mel-frequency-based Cepstral coefficients in a time window of a specific length at periodic intervals. Each set of measuring data consists of a series of feature vectors measured. Each audio file is specified by the complete set of the feature sequences calculated for each feature. In addition, the first derivations are calculated for each sequence of feature vectors. Then statistical values such as the mean value and the standard deviation are calculated. This set of values is stored in an N vector, i.e. a vector with n elements. This procedure is applied to a plurality of audio files to derive an N vector for each audio file. In doing so, a database is gradually built from a plurality of N vectors. A search N vector is then extracted from an unknown audio file using the same procedure. In a search enquiry, a calculation of the distance of the specified N vector and the N vectors stored in the database is then determined. Finally, that N vector which is at the minimum distance from the search N vector is output. The N vector output has data about the author, the title, the supply source, etc. associated with it, so that an audio file may be identified with regard to its origin.

The disadvantage of this method is that several features are calculated, and arbitrary heuristics may be introduced for calculating the characteristic quantities. By mean-value and standard-deviation calculation across all feature vectors for one whole audio file, the information being given by the feature vector's temporal form is reduced to a few feature quantities. This leads to a high information loss.

Prior art methods for a sound signal analysis are, therefore, disadvantageous in that they all rely on a certain kind of time/frequency transform or on a kind of time or frequency pattern recognition etc. All these algorithms either completely ignore the fact that the receiver of the sound signal is a human being or include this fact only to a small degree into a sound analysis procedure. Although it is known from audio-signal compression techniques which are based on a psycho-acoustic model that sound signals include a huge amount of irrelevant portion, i.e., sound signal information, which is not used by the human being for audio recognition, the prior art methods for sound signal analysis ignore such things. Although one might consider to perform a music analysis on signals, from which irrelevant portions have been removed such as by means of a quantization procedure based on a perceptual model, such concepts also are problematic in that they are not consequently driven by the fact that—in the final analysis—the solely intended receiver for music is a human being rather than a computer or a sound signal data base etc.

SUMMARY OF THE INVENTION

It is the object of the present invention to provide a more accurate concept for a sound signal analysis.

In accordance with a first aspect of the present invention, this object is achieved by an apparatus for analyzing a sound signal, comprising: an ear model for deriving, for a number of inner hair cells, an estimate for a time-varying concentration of a transmitter substance inside a cleft between an inner hair cell and an associated auditory nerve from the sound signal, so that an estimated inner hair cell cleft contents map over time is obtained; and a pitch analyzer for analyzing the cleft contents map to obtain a pitch line over time, a pitch line indicating a pitch of the sound signal for respective time instants.

In accordance with a second aspect of the present invention, this object is achieved by a method of analyzing a sound signal, comprising the following steps: deriving, for a number of inner hair cells, an estimate for a time-varying concentration of a transmitter substance inside a cleft between an inner hair cell and an associated auditory nerve from the sound signal, so that an estimated inner hair cell cleft contents map over time is obtained; and analyzing the cleft contents map to obtain a pitch line over time, a pitch line indicating a pitch of the sound signal for respective time instants.

In accordance with a third aspect of the present invention, this object is achieved by a computer program having instructions being operative for performing the method of analyzing a sound signal when the program runs on a computer.

The present invention is based on the finding that an accurate and human being-related sound analysis is obtained by performing a pitch analysis and a rhythm analysis and/or a timbre recognition based on estimates for time/varying concentrations of a transmitter substance inside a cleft between an inner hair cell and an associated auditory nerve. It has been discovered that the transmitter concentration in a cleft between an inner hair cell of the human ear and an associated auditory nerve is decisive for sound recognition which is done within the human being's brain. Up to the transmitter concentration, i.e., from the outer ear through the middle ear until the inner ear, there is a lot of non-linear sound processing performed by a certain shaping of the respective parts within the ear and the resonance characteristics of the certain mechanical components. Then, the inner hair cells are responsible for doing a kind of a mechanical-to-electrical-conversion by determining the transmitter concentration in the cleft between an inner hair cell and an associated auditory nerve.

It has been found out that the inner hair cells, which are coupled to respective areas of the basilar membrane within the inner ear are "phase-locked" to the vibration of the basilar membrane. Thus, a time-varying transmitter concentration has the same vibration period as the respective area of the basilar membrane exciting the inner hair cell.

This characteristic is used for the purposes of the present invention when a pitch line over time is derived from the estimates for the time-varying transmitter concentration.

Additionally, it has been found out that the envelope of the transmitter concentration is very significant for identifying changes within a music signal, for example. It has been found out that an onset of the transmitter concentration after a quiet period is much higher than an onset after a not so quiet period.

Therefore, the characteristic of the transmitter concentration is an excellent measure for performing rhythm and pitch analysis. this is due to the fact that the transmitter concentration has a clean stationary part, when the music signal is stationary within, for example, a single note. The transmitter concentration estimate, however, has also a very prominent envelope indicating a change from a preceding note to a succeeding note.

It has been found out that these characteristics are very advantageous for performing a rhythm analysis so that an inventive rhythm analyzer makes use of certain transmitter concentration envelopes identified by the pitch line to perform segmentation of a pitch line to find out rhythm information of a music signal (in addition to the pitch line information which has been found out by the inventive pitch analyzer). The inventive device is, therefore, operative to extract pitch line information as well as rhythm information from a sound signal so that the inventive device can perform a transcription into several formats such as the well-known note description or an MIDI description which is suitable for being input into an electronic musical instrument such as a keyboard or a sound processor card of a computer so that the analyzed sound can be reproduced.

Alternatively, the inventive device is also appropriate for performing a music recognition based on feature vectors derived from the estimates for time-varying concentrations of transmitter substances within clefts between inner hair cells and associated auditory nerves. this method is based on a feature vector analysis and data base retriever using features derived from the estimated inner hair cell cleft contents map over time.

To summarize, the inventive device is advantageous in that it relies on inner hair cell-produced transmitter concentrations. Representations of resulting mechanical vibrations of basilar membrane and lymphatic fluids are fed into the inner hair cell model, where the incoming signal is transformed into neural impulses. The resulting concentration of transmitter substance inside the cleft between a hair cell and an associated auditory nerve is used for the inventive pitch and the rhythm analysis. By using the inner hair cell model, most of the measurable transduction processes are acknowledged for in the inventive concept. Therefore, the inventive device proves to be a suitable choice for musical sound processing.

Pitch perception is the fundamental human access to melodic evaluation of musical input. Therefore, the inventive concept provides a strategy for extracting fundamental frequency data from the sound signal or, what is even more important, perceived frequencies. The auditory periphery uses, in accordance with the present invention, the so-called "phase-locking" phenomenon. Because of a variable mechanical inertia and stiffnesses of basilar membrane sections characteristic resonance frequencies can be attached to every inner hair cell position.

The distribution of characteristic frequencies shows a tonotopic behavior, i.e., that low frequencies are assigned to low inner hair cell numbers etc. The inner hair cells preserve frequency information by producing neural firings at precise moments of the stimulating wave they are responding to. This results in time-varying concentrations of transmitter substances inside the clefts between inner hair cells and the associated auditory nerves, which have the two advantageous characteristics, i.e., a time-varying concentration having the same fundamental and higher partial vibration frequencies as the associated portion of the basilar membrane, and additionally a very significant envelope strongly indicating a non-stationary part within the sound signal, i.e., a change from one note to another note, which change being indicative for the rhythm underlying the sound signal.

BRIEF DESCRIPTION OF THE DRAWINGS

Preferred embodiments of the present invention are described in details with respect to the accompanying drawings, in which:

FIG. 1 shows a sample score in a conventional note description;

FIG. 2 shows a sound wave belonging to the sample score in FIG. 1;

FIG. 3 shows an estimated inner hair cell cleft content map over time;

FIG. 4 indicates an estimate for a time-varying concentration of a transmitter substance inside a cleft between inner hair cell number 12 and an associated auditory nerve for two different time resolutions;

FIG. 5 shows an estimate for a time-varying concentration of transmitter substance inside a cleft between inner hair cell number 25 and an associated auditory nerve for two different time resolutions;

FIG. 6 shows a sample SACF histogram for a certain point in time, indicating the fundamental vibration and some higher partial vibrations;

FIG. 7 indicates a "raw" pitch line and a processed pitch line, from which potential artifact data have been removed;

FIG. 8 indicates envelopes of transmitter substances for the first partial (fundamental vibration) and the fourth partial for transmitter concentration estimates of inner hair cells selected in accordance with the pitch line from FIG. 7;

FIG. 9 indicates an onset map in a three-dimensional and a two dimensional representation;

FIG. 10 indicates an onset masking procedure for removing "double onsets" from FIG. 9;

FIG. 11 indicates an onset histogram;

FIG. 12 indicates a segmented pitch line including melody and rhythm information from the original sound signal shown in FIG. 1;

FIG. 13 indicates feature values for timbre recognition for a clarinet;

FIG. 14 indicates results for a query-by-humming for several analysis methods;

FIG. 15 indicates results for a query-by-humming process including GSM distortion for several methods;

FIG. 16 indicates results for a timbre recognition for several different recognition processes;

FIG. 17 indicates a schematic of the extended analog model by Baumgarte;

FIG. 18 indicates a hair cell model by Meddis;

FIG. 19 shows a mathematic description of the Meddis model from FIG. 18;

FIG. 20 indicates a cross-section of the cochlea;

FIG. 22 indicates a preferred embodiment of the inventive pitch analyzer of FIG. 21; and FIG. 23 indicates a preferred embodiment of the inventive rhythm analyzer of FIG. 21.

DETAILED DESCRIPTION OF PREFERRED EMBODIMENTS

Figure 21:
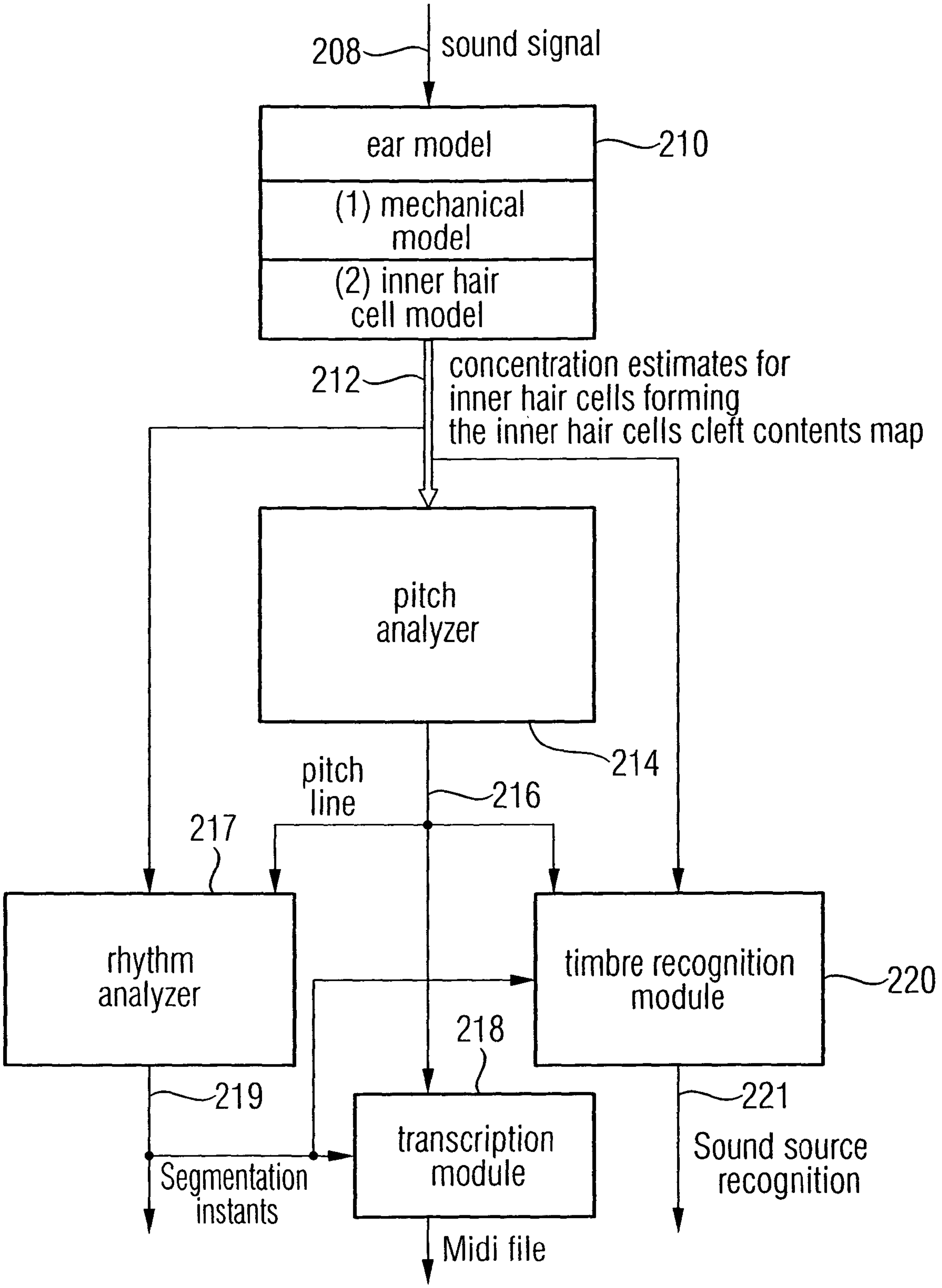
FIG. 21 shows a block diagram of the inventive sound signal analyzing apparatus in accordance with the preferred embodiment of the present invention.

FIG. 21 shows a preferred embodiment of an inventive apparatus for analyzing a sound signal such as a sound signal shown in FIG. 1.

The inventive device includes an ear model 210. The ear model is operative to derive, from the sound signal at the sound signal input 208, an estimate for a time-varying concentration of a transmitter substance inside a cleft between an inner hair cell and an associated auditory nerve so that concentration estimates for inner hair cells are obtained which form the inner hair cell cleft content map, which is indicated at the ear model output 212 in FIG. 21. An example for an inner hair cell cleft content map is shown in FIG. 3. FIG. 3 indicates estimated transmitter concentrations over time (from 0 seconds to 0.28 seconds for exactly 251 inner hair cells). As has been outlined above, lower order inner hair cells indicate lower frequencies, while higher order inner hair cells indicate higher frequencies. In particular, each inner hair cell is preferably associated with a unique area of the basilar membrane. The basilar membrane is divided into 251 such areas of uniform widths which result in a resolution of 0.1 Bark. Every basilar membrane segment is connected to one inner hair cell, which is fed with vibrations of the corresponding basilar membrane section.

The data at output 212 are input into a pitch analyzer block 214. The pitch analyzer is operative to analyze the cleft contents map (of, for example, FIG. 3) to obtain a pitch line over time (FIG. 7), wherein the pitch line indicates a pitch of the sound signal for respective time instants.

Preferably, the inventive analyzing apparatus further comprises a rhythm analyzer 217 which is operative to analyze envelopes of estimates for selected inner hair cells, the inner hair cells being selected in accordance with a pitch line output at pitch analyzer output so that segmentation instants are obtained, wherein a segmentation instant indicates an end of a preceding note or a start of a succeeding note. Segmentation instants are shown as vertical lines in FIG. 12, wherein FIG. 12, altogether, shows the result of pitch and rhythm analysis which can be input into a transcription module 218. As can be seen in FIG. 21, a transcription module 218 receives the pitch line at output 216 and the segmentation instants output at rhythm analyzer output 219.

Another embodiment of the present invention also includes a timbre recognition module 220, which provides a sound source recognition information at output 221. The timbre recognition is operative for constructing a feature vector based on the pitch line 216 and, preferable, based on segmentation instants output by block 217. Additionally, module 220 is operative for obtaining a result indicating the probability that at least a portion of the sound signal has been produced by a sound source from a number of different specified sound sources.

Preferably, a module 220 includes a neural network and includes as a feature group several features which are described below with respect to FIG. 16.

In the following, a preferred embodiment of the pitch analyzer 214 in FIG. 21 is described with respect to FIG. 22. Preferably, the pitch analyzer includes a vibration period detector for each transmitter concentration estimate 214*a*. The vibration period detector 214*a* is operative to build a sequence of summary auto correlation function (SACF) histograms. To this end, the vibration period detector preferably uses a certain time period from a single transmitter concentration estimate such as for inner hair cell number 12 in FIG. 4 or for inner hair cell number 25 in FIG. 5. Preferably, the vibration period detector excludes, for example, a period of 50 ms from each inner hair cell concentration estimate and derives the time distance T between two adjacent maxima for a certain number of specified maxima.

When, for example, the inner hair cell concentration estimate of FIG. 4 is completely evaluated by calculating six values T, these six values T can be introduced into the summary auto correlation function histogram in FIG. 6.

The same procedure can be performed for inner hair cell concentration estimate number 25. When the whole FIG. 5 time period would be used, thirteen values for T could be introduced into the histogram.

In the end, when all 251 inner hair cell concentration estimates are processed for a certain time period, one obtains FIG. 6 showing a short-time frequency distribution of the sound signal perceived by the human ear. This processing will result in a sequence of histograms output by block 214*a* in FIG. 22. Then, the sequence of SACF histograms is input into a maximum value extractor 214*b*, which extracts the first maximum from each histogram. This will result in the extraction of a value of about 100 Hz for the time period shown in FIG. 4 and FIG. 5 (pictures to the right side). The fundamental or pitch frequency for the first 100 ms of the sample score from FIG. 1 is 100 Hz. Additionally, one can see lower valued (but still significant) maxima for the second partial at a frequency a little bit lower than 200 Hz, the third partial and the fourth partial.

The maximum value extractor 214*b* will output pitch line points which are shown in the left picture of FIG. 7. The FIG. 7 data will be input into a subtrajectory builder 214*c*, which is operative to build pitch subtrajectories as indicated below. Finally, the pitch subtrajectories output at block 214*c* are input into a fuser and discarder block 214*d* for outputting a cleaned pitch line as indicated in the right picture of FIG. 7.

Stated in other words, the pitch analyzer is operative to output for each time period, for which the FIG. 6 histogram is produced, the frequency of the vibration mode, in which most of the inner hair cells vibrate.

At this point it should be noticed that the basilar membrane is a membrane which, of course, has certain areas or segments which have a certain "main frequency". However, the basilar membrane cannot vibrate such that one portion heavily vibrates, while the neighboring portion does not vibrate at all. This means that one cannot say that every inner hair cell has associated therewith a certain frequency value. To the contrary, it has been found out, that, for the considered case of a vibration with 100 Hz, inner hair cell number 12 vibrates, and also several neighboring inner hair cells will also vibrate with the same frequency but with a lower amplitude.

Therefore, as soon as a maximum value of the SACF histogram for a certain time period is extracted, one can find a dominant concentration estimate for a certain inner hair cell, i.e., the selected inner hair cell which vibrates with the vibration frequency obtained by the SACF histogram. Naturally, there will be more than one inner hair cells vibrating with this frequency. The dominant inner hair cell is, however, the inner hair cell which has the largest amplitude among the inner hair cells resonating with the same vibration frequency.

This information will be used later on for the purposes of rhythm analysis, when envelopes will be considered for finding segmentation instants or segmentation points for segmenting the pitch line found out by the pitch analyzer.

With reference to FIG. 23, this search for dominant estimates having a pitch is done by a searcher 217*a* shown in FIG. 23. As an input, block 217*a* receives the cleft contents map 212 and the pitch line 216.

Preferably, element 217*a* is operative to not only consider the fundamental vibration mode at, for example, 100 Hz but also higher partials such as the second, third, fourth and fifth partials.

It has been found out that the significance of the rhythm information results for the eventually obtained segmentation information can be improved when one or preferably more higher partials are considered in addition of instead of only the fundamental frequency mode. This becomes clear from FIG. 8. Here, it is visible that segmentation information is much more clearer in the fourth partial compared to the first partial (the left picture of FIG. 8), which corresponds to the fundamental vibration mode.

To this end, the searcher 217*a* shown in FIG. 23 is not only operative to search for dominant estimates having the pitch frequency over time but to also search for dominant estimates having higher partials frequencies in order to build more than one envelopes of transmitter substance as shown in FIG. 8.

It is to be noted here that, when the pitch line in FIG. 7 and the cleft content in FIG. 8 are considered, FIG. 8 does not show a single estimate for a single hair cell throughout the first 5 seconds of the music's score. Instead, FIG. 8 shows assembled data from the respective inner hair cell clefts, which have the frequencies (higher harmonics) as indicated in FIG. 7. Therefore, FIG. 8 indicates a serially assembled collection of dominant estimates.

In particular, the procedure to build the FIG. 8 picture works as follows. First of all, an SACF histogram (FIG. 6) is built for let's say the first 100 ms of the sound signal. Then, the dominant inner hair cell estimate is searched as outlined above. Then, this procedure is repeated for higher partials. Then, the first 100 ms of the dominant estimates for each partial are input into a diagram for each partial to obtain the first 100 ms of the FIG. 8 picture. Then, the same procedure is repeated for the second 100 ms. Again, another SACF histogram is build and another search for dominant estimates for the fundamental mode and the higher partial modes is performed. When a dominant estimate for each mode has been found, the respective second 100 ms from each dominant estimate are entered into the FIG. 8 diagrams for each partial. This procedure is repeated until, for example, the first six seconds of the sound signal are processed in this regard. Then, this information can be used, since it already includes the envelope information. Alternatively, one can process these data to find a real envelope by, for example, connecting maxima and minima etc.

Then, the FIG. 8 data are input into an onset map builder 217*b*, which builds an onset map as shown in FIG. 9. Then, the FIG. 9 data are processed by an onset histogram builder 217*c*, which preferably performs a "double onset" rejection as will be outlined later.

Finally, block 217*d* termed "maximum extractor" processes the onset histogram output by FIG. 11 to output the vertical segmentation lines, which are shown in FIG. 12. These segmentation lines respectively indicate an end of a preceding note or a start of a succeeding note.

In the following, a preferred embodiment of an ear model (210 in FIG. 21) will be shown with respect to FIGS. 17 to 20 in order to derive the inner hair cell cleft contents map from the sound signal in an accurate and effective way.

In accordance with a preferred embodiment of the present invention, the so-called "extended analog model" authored by F. Baumgarte, "*Ein psychophysiologisches Gehoermodell zur Nachbildung von Wahrnehmungsschwellen fuer die Audiocodierung*", Dissertation, University Hanover, 2000 is shown. This analog model is used for modeling auditive perception thresholds. The description of the inner hair cells in the Baumgarte model is replaced by the Meddis inner hair cell model which has been found as best performing compared to other inner hair cell models. In particular as has been outlined above, the so-called phase-locking model for implementing the human frequency and pitch perception is included.

The model shown in FIG. 17 models the outer ear and the middle ear as a linear filter. Because of the normally unknown sound incidence direction, an "average" transfer function is assumed. Below a frequency of about 1 kHz, one has a rise of 6 dB per octave. The significant auditory resonance contributes to a resonance gain at about 3 kHz. Above this frequency, one has a constant filter function.

This model is implemented as a passive electric network. The description of the hydro-mechanic elements of the inner ear as well as the outer hair cells can be done using the well-known extended analog model by Zwicker and Peisl. Here, one has a one-dimensional representation of the cochlea, i.e., the influence of radial and axial positions is neglected without a significant loss of accuracy. A cross-section of the cochlea is shown in FIG. 20, in which the auditory nerves, the outer hair cells and, particularly, the inner hair cells near the basilar membrane are shown. It is to be noted here that the clefts are arranged between the auditory nerves and the inner hair cells, and the transmitter concentration within these clefts form the inner hair cell cleft contents map over time which is used for sound signal analysis in accordance with the present invention.

As will be outlined later on, the mechanical portions of the model allow a simulation of the frequency-location-transform which is performed within the inner ear. Additionally, the frequency selectivity which accompanies the frequency-location-transform can also be accounted for. By means of active and non-linear elements, the amplification effect of the outer hair cells which are responsible for dynamic compression, distortion products and suppression, are modeled. The model preferably includes 251 identical serially connected sections which represent small longitudinal segments of the cochlea. The tonality distance between adjacent segments is, therefore, about 0.1 Bark. The sub units can be formulated as a system of coupled differential equations. The use of electro-acoustical analogies allow a representation as an electric network consisting of concentrated elements. The resulting schematic of a cochlear segment is shown in FIG. 17. With respect to hydro-mechanics, the parallel resonance circuit models stiffness, mass and friction losses of the cochlear separation wall. The other element describe mass and associated friction losses of the longitudinally moved lymphatic fluid.

The active and non-linear behavior of the outer hair cells, which results in an amplification of the basilar membrane threshold is modeled as a voltage controlled voltage source having a point-symmetric saturation characteristic curve. Within the feedback loop, the output signal is fed back into the hydro-mechanic part. The coupling resistors model the lateral coupling of certain sections over the outer hair cells.

The second amplifier stage consisting of a current source and the parallel resonance circuit is used for avoiding instabilities at high amplification values. The simulation is performed with the help of so-called wave digital filters (WDF) in the time domain. This results in a good time resolution which is advantageous for a good signal segmentation.

At the outputs of the several sections of the Baumgarte model, a description of an inner hair cell is connected to. The limited number of sections along the basilar membrane models the performance of neighbored hair cells or nerve populations.

The preferred Meddis model is based on a probability description of the transduction processes. A basic assumption is that the amount of transmitter substance within the synaptic cleft is a function of the stimulating intensity. Additionally, the probability for triggering an action potential on the auditory nerves is proportional to the concentration of the transmitter substance inside the cleft.

FIG. 18 shows a schematic description of this model. The transmitter substance is exchanged between different reservoirs depending on the levels of present concentrations and the levels of the input stimuli. The main parameter for the diffusion of transmitter substance from the hair cell into the synaptic cleft is the permeability of the hair cell membrane which is given through the membrane permeability k shown at the top in FIG. 19. The parameter A describes a lowest excitation amplitude, at which the membrane becomes permeable. B determines the first derivative of the permeability curve, while S indicates the stimulus intensity. The stimulus clock is determined through the infinitesimal time interval dt.

q stands for the free transmitter within the hair cell. Then, kqdt is the transmitter amount which is input into the synaptic cleft per simulation clock. It is to be noted here that a portion of the transmitter concentration c gets lost within the cleft (lc), while another portion is recirculated (rc) and will be used in another excitation process (xw). Within the "new fabrication" reservoir, a new transmitter is produced, which compensates for substance losses depending on the present concentration. These processes can be modeled by means of a system of differential equations as shown in FIG. 19. The preferred values for the respective model parameters are also shown in FIG. 19.

As has been outlined above, the ear uses a kind of encoding of frequency contents of a sound signal using a tonotopic mapping of portions along the basilar membrane within the inner ear. This functionality which is also called a frequency-location-transform is influenced by several non-linear characteristics of the inner ear at characteristic locations which result in resonant vibrations. Nevertheless, this position-dependent encoding of the spectral contents is not sufficient for the huge amount of practical sound signals. When a background noise is present, this characteristic local resonance pattern is almost completely hidden. Additionally, the excitation of associated basilar membrane regions is almost completely constant for very low but still audible frequencies.

The term "phase-locking" is known in the art as the coupling the triggering of action potentials depending on the phase situation of the sound oscillations. Therefore, the spectral information is encoded within the inner ear not only spectrally but also in a time manner. Based on pause-lengths between single action potentials of groups of action potentials, the frequency of the exciting vibration can be determined. This frequency is inversely proportional to the period of the sound signal. It is known in the art that this mechanism is decisive for sound perception. The preferred pitch line analyzer is based on this physical effect.

One can consider the inner hair cell processing as a halfway rectification. The inner hair cells and the stereociles positioned on the inner hair cells result in a depolarization and ejection of transmitter substance only when an excitation in a single direction takes place. A stimulus triggering preferably takes place at the maximum of a half-phase, i.e., at an excitation of the cochlear separation wall and the stereociles in the stimulating direction.

In the following, the preferred embodiment of the present invention is described with respect to FIGS. 1 to 16.

The presented invention applies the basic preprocessing steps, as used by mammalian auditory periphery, for analyzing musical inputs. The chosen model proves to be suitable because of its implicit good spectral and temporal resolution.

Practical applicability is evaluated in the context of the implementation of a Query-By-Humming system, i.e. a user inputs a query melody (by means of singing or playing an instrument) to a search engine. This input, internally represented as a waveform signal, is then analyzed and transformed into a high-level sequence of musical notes. The result is compared with a reference transcription given by a MIDI database; a list of the most similar entries is presented to the user as a result.

As a second case study, an analysis of woodwind instrument sounds is conducted to demonstrate how to mimic other human pattern recognition capabilities. It is shown how characteristic features of different musical instruments can be extracted and how they are used for classifying the involved sound sources with respect to their original instrument families.

As an alternative to commonly used (perceptually justified) filterbanks the extended "Analogmodell" by Zwicker (E. Zwicker, H. Fastl, Psychoacoustics, Springer, pp. 23-60, 1999) is used to mimic the active functionality of the mammalian auditory periphery. The mechanical sound processing up to the inner ear (cochlea) is modeled. Nonlinear characteristics of the outer hair cells are included as they are responsible for a number of auditory effects (adaptive filtering, otoacoustic emissions, etc.)

Representations of resulting mechanical vibrations of basilar membrane and lymphatic fluids are fed into the inner hair cell model (IHC) described in R. Meddis, *Simulation of mechanical to neural transduction in the auditory receptor*, JASA, 79(3), pp. 702-711, 1986, or R. *Meddis Simulation of auditory-neural transductions: Further studies*, JASA, 83(3), pp. 1056-1063, 1988. Here, the incoming signal is transformed into neural impulses. The resulting concentration of transmitter substance inside the cleft between hair cells and auditory nerves is used in the subsequent analysis steps. The IHC model describes most of the measurable transduction processes. In comparison to other available approaches M. J. Hewitt, R. Meddis, *An evaluation of eight computer models of mammalian inner haircell function*, JASA, 90(2), pp. 904-

917, 1991) and as far as the needed accuracy is concerned, the model proves to be a suitable choice for musical sound processing.

Pitch perception is the fundamental human access to melodic evaluation of musical input. Therefore a strategy is needed to extract fundamental frequency data from the audio signal, or, that is more important, perceived frequencies, respectively. Auditory periphery uses so called "phase locking": because of variable mechanical inertia and stiffnesses of basilar membrane sections characteristic resonance frequencies can be attached to every IHC position. Distribution of characteristic frequencies shows tonotopic behavior (low frequencies are assigned to low IHC numbers, etc.). IHCs preserve frequency information by producing neural firings at precise moments of the stimulating wave they are responding to. This is valid for frequencies up to 5 kHz and is thereby sufficient as a pitch extraction method for practically all musical signals.

The inventive rhythm analysis uses psychological and psychoacoustic knowledge as it is suggested by A. Klapuri, Sound onset detection by applying psychoacoustic knowledge, Proceedings of the IEEE ICASSP, Phoenix, Ariz., 1999, to segment previously calculated pitch trajectories into single musical notes. Features like the well known Weber fraction (describing small noticeable changes in intensity), or temporal pre- and postmasking effects are adapted.

As to timbre recognition, it is outlined that the present invention is interested in imitating human perceptive strategies. So, the exemplary use of those transient parameters to extract timbre information is performed. Proceedings of the first partials of involved sound sources are extracted by the ear model. The received information is represented in a feature vector. This is fed into a known neural network for training and pattern recognition processes.

Based on the work of Baumgarte as cited earlier the extended "Analogmodell" is implemented with wave digital filters (WDF) in the time domain. This requires a remarkable amount of computational power: after optimization a 2 GHz PC needs two seconds computational time for a one second input. The drawback in efficiency is, however, compensated by an excellent time resolution as it shows to be necessary for a reliable segmentation of single notes and description of timbres. The basilar membrane is divided into 251 areas of uniform width, i.e. a resolution of 0.1 Bark. Every segment is connected to one IHC, which is fed with the vibrations of its corresponding section. The IHC model shows good computational efficiency and can be described by a number of simple differential equations as outlined in R. Meddis, M. J. Hewitt, T. M. Shackleton, *Implementation details of the inner hair-cell/auditory-nerve synapse*, JASA, 87(4), pp. 1813-1816, 1990.

Subsequently, the implementation details of the present work will be illustrated using an exemplary melody input (see FIG. 1 and FIG. 2 for the score and a voiced input of the main melody of S. Prokofiew's "Peter and the wolf".

The preferred pitch extraction method to form resulting pitch trajectories, i.e. continuous courses of pitch values, is demonstrated using the first note of the input. The temporal evolution of the envelopes of the 251 IHC cleft contents along the basilar membrane are shown in FIG. 3. Certain structures of harmonic partials can be seen, but the description is not sufficient for an exact calculation of the frequencies of the partial tones present in the input signal. FIG. 4 and FIG. 5 contain detailed illustrations of the cleft contents for those IHCs which are located in areas corresponding to the frequencies of the stimulating partials. IHC #12 is in resonance with the fundamental frequency, whereas IHC #25 represents the second partial. Interference effects according to the fundamental frequency can be seen for the second partial as an illustration of spectral masking effects, i.e. alternating amplitudes of cleft content maxima occur. Every second maximum results from the sum of vibrations of the fundamental and the second partial.

Because of the above described properties of phase locking, the time difference between subsequent maxima of cleft contents corresponds to the period of the actual vibration. The reciprocal value determines the according frequency.

Now all time deltas between one maximum and its first 7 neighbors are entered into a histogram using the sum of the two involved maxima amplitudes as weight value. This is repeated for the next 10 succeeding maxima and their corresponding neighbors. This process results in a so called summary autocorrelation function (SACF) as described in R. Meddis, M. J. Hewitt, *Virtual pitch and phase sensitivity of a computer model of the auditory periphery. I: Pitch identification*, JASA, 89(6), pp. 2866-2882, 1991, or R. Meddis, R., L. O'Mard, *Psychophysically Faithful methods for Extracting pitch*, in Computational Auditory Scene Analysis, D. F. Rosenthal, H. G. Okuno, (eds), Lawrence Erlbaum Associates, pp. 43-58, 1998 [23][24].

A resulting picture like that in FIG. 6 can be found. The maximum histogram value undoubtedly represents the fundamental frequency of the sung input. Other less definitive cases require more sophisticated considerations about relationship between the significant maxima occurring in the histogram. After calculating SACF histograms for every millisecond of the input signal, an estimate of the most significant pitch can be found for every point in time (see FIG. 7). Considering continuity relationships between succeeding pitch estimations so called pitch trajectories are built. For this purpose, pitch values which are close in time and frequency are combined to form subtrajectories. In a next step, subtrajectories with a minimum length and more global proximity are fused to pitch trajectories. If length and amplitude values of those general pitch sequences exceed some predefined thresholds, corresponding trajectories are saved as valid. These processing steps remove most of the noisy pitch entries and a clean course of pitches is left (see FIG. 7).

Pitch extraction is handled well by many different conventional methods. As far as a reliable segmentation of the extracted pitch trajectories into single musical notes is concerned, however, satisfying results cannot be obtained in most cases. The advantageous trade-off between temporal and spectral resolution provided by the chosen approach enables a procedure to a reliable segmentation method. For this purpose envelopes of transmitter substance inside the IHC clefts for the first 7 partials are considered (see FIG. 8 for the $1^{st}$ and $4^{th}$ partial). The procedure searches for steep and strong increases giving indicators for beginnings of new events, as shown in R. Meddis, *Simulation of mechanical to neural transduction in the auditory receptor*, JASA, 79(3), pp. 702-711, 1986, or R. Meddis *Simulation of auditory-neural transductions: Further studies*, JASA, 83(3), pp. 1056-1063, 1988.

IHCs strongly react to new stimulations as some kind of alert system. Once significant increases of cleft content were found, the law of a constant Weber fraction is applied, i.e. the increment in signal amplitude is evaluated in relation to its level as outlined in the Klapuri reference. The detected strong rise is assigned a value Δcct/cct (Δcct is the amplitude increment and cct is the starting value of the cleft content amplitude for that onset). Thus we calculate a relative measure of perceived change in signal intensity; the same amount of increase appears to be more prominent in a quiet signal.

Therefore increases starting at a high level are assigned less importance in the segmentation process.

Valid onset portions exceeding a predefined threshold are fed into the so called "onset map" (see FIG. 9). After that the onset map is scanned using windows of suitable width; simultaneous entries are summed up in an "onset histogram" (see FIG. 11). The next task is to find maxima above certain onset thresholds, but a serious problem arises doing that. often "double onsets" are found, i.e. at the beginning of voiced syllables more than one onset is detected. FIG. 3 illustrates a typical constellation where the first note of the input melody is articulated as the syllable "na". There is a clear segregation between the two phonems "n" and "a". Steep increases of cleft content in broad partial areas can be found both for the "n" and the "a". The length of those typical voiced nasal consonants like the "n" often continues up to some 100 milliseconds. Therefore many segmentation approaches will report two note onsets (rather than a single one). Adaptation of pre- and postmasking effects borrowed from known psychoacoustic models can eliminate the problem in most cases. A fusion of very near neighbored onsets is introduced (distance smaller than 75 milliseconds (see FIG. 10)). Additionally adjacent areas are considered where onsets with values below a gliding threshold are dismissed.

All maxima of the smoothed and "double onset" cleaned histogram exceeding carefully defined thresholds determine note onsets produced by significant rises in the envelopes of the IHC transmitter substance. Supplementary pitch based postprocessing segmentation steps are introduced which are needed e.g. to find gliding note transitions that cannot be found with the described onset segmentation procedures. Pitch trajectories and note onsets (i.e. the final result of the segmentation process) are shown in FIG. 12.

A calculation of note offsets is dismissed here for different reasons. On one hand, room acoustic often blurs clear offsets by introducing echo effects thus decreasing the reliability of offset detection. On the other hand, it was assumed here that the note onsets constitute the most important parameters enabling a rhythmical interpretation of perceived musical content. Consequently, offsets are attached to the beginning of the following note onset for continuing pitch trajectories, otherwise to the end of the trajectory, respectively.

While the main application of the inventive system was put on the automatic transcription of melody in musical inputs, the analysis of timbre information in sound signals is another interesting application. It is planned to benefit from this in polyphonic sounds to extract auditory streams or to identify performing singers.

As an example for the possible use, some woodwind instruments are analyzed to show the viability of the chosen approach. More specifically, clarinet, bassoon and oboe instruments are considered as a small set of instruments which limits the necessary amount of training data to a reasonable size.

While other instrument families like strings possess very different timbres and occupy distinct spheres in the feature space, the chosen woodwind instruments show very similar timbral qualities. Thus, a success application to the woodwind instrument set would constitute a good basis to generalize the inventive method to a more complete set of instruments.

The main contribution to the perceived timbre is attributed to the transient portion at the beginnings of musical notes. The present work confines the used features for pattern recognition to these starting areas although the use of data from stationary signal portions would further improve the performance of technical system.

FIG. 13 shows the used parameter for an example note performed by a Bb clarinet playing Bb3, i.e. ~236 Hz. The rows include values for the first seven partials.

The second column represents the times of partial cleft content envelopes reaching their maxima. Characteristic relations between the time differences can be found for different instruments. Calculating the differences between higher partials and the fundamental 6 feature values can be extracted.

The second set of features can be found in column three. Partial frequencies at maximum time are illustrated. Relations of higher partials and the fundamental are built and again 6 new feature values arise. In this particular case a deviation of partial frequencies from the ideal integer relationship of harmonics can be seen: a slight deviation downwards for the higher partials can be recognized. String instruments e.g. would show a quite different behavior because of the involved stiffnesses and inertia; the strings increasingly show problems following the stimulating frequencies of higher partials. More significant deviations result and can thus be used as instrument recognition patterns.

Amplitudes of the maxima constitute the third group of features as found in column 4. Characteristic relative combinations of fundamental and higher partials yield 6 new parameters.

Furthermore the position of the best resonating IHCs and the width of resonances regarding to the number of vibrating IHCs are used as absolute values (column 5 and 6). The size of the feature vector is therefore incremented by 14 new entries. Finally the overall pitch estimate of the considered note is added to the feature vector; this gives a total size of 33 recognition parameters. The resulting information is fed into a neural network. The pattern recognition is implemented as a "multilayer perceptron". Four layers of neurons are used. The input layer consists of 33 neurons corresponding to the total number of the relative and absolute feature values. The hidden layers consist of 20 neurons each. Three neurons representing the considered instruments (oboe, bassoon and clarinet) are located in the output layer. The training process is carried out in supervised mode and involves 60000 steps. After several seconds of training, the error is less than 0.01 (using standard error backpropagation).

The functionality and robustness of the chosen algorithm has been tested extensively by informal "Query-by-Humming" queries and subsequent transcription of the melody query inputs. Using dynamic programming these inputs were searched for in a MIDI database were reference transcriptions are provided. A list of the ten most similar search results was given. In the statistical evaluations the Top1 and Top10 scores are illustrated as a measure of performance quality, indicating the percentage of occurrence for the correct item within the first and first 10 most closest matches, respectively.

A number of different sound sources reaching from singing voice input in different articulations to various musical instruments were used. Recordings were made in the surroundings of an exhibition hall. Thus, a significant amount of environmental noise interference is included in the test signals.

A total of 1152 query inputs including a wide quality range (professional vs. amateur) were evaluated.

The inventive method ("EarAnalyzer") was tested in comparison to two other conventional algorithms. While the first of the alternative approaches was implemented working directly on the extremal sound sample values ("Extreme"), the other used a Hough ("Hough") transform for extracting pitch.

In FIG. 14 the test results are shown. Two databases with different sizes (200 and 1024 entries) were tested. Because of the increasing self-similarity between the reference melodies for larger databases, the results become worse for the second (larger) database. A much higher loss in recognition performance is, however, visible when using the alternative methods as compared to the performance of the inventive scheme. Apparently, the new method provides a more accurate description of the analyzed melodies.

In both cases the "EarAnalyzer" approach performed significantly superior to the conventional methods, showing an improvement in recognition rate of at least 17 percent. A second test was executed applying the three algorithms to GSM mobile phone distorted signals. For this purpose the original 1152 input data have been processed by different speech coding techniques used for mobile telephony (GSM full rate, enhanced full rate and half rate). Again, the superior performance of the chosen physiological model can be observed.

In summary, the inventive physiological approach shows very good performance in the environment of a "Query-By-Humming" system. Even poor musical inputs regarding to incorrect intervals and rhythmical structure can be found in a reference database. Additionally it proves to be robust against noise interference and GSM distortions. Therefore suitability for a commercial application can be expected.

Furthermore, the performance as a sound source recognition method was evaluated using different training and test datasets consisting of single notes and melodies performed by woodwind instruments. Three different test datasets were used. Two professional inputs provided by the universities of Mc Gill and Gdansk and one amateur dataset recorded by the authors were analyzed. Each dataset consists of following instruments and note ranges:

clarinet: 36 notes (D#3-D6)
oboe: 30 notes (C4-F6)
bassoon: 32 notes (A#1-F4)

This gives a total of 294 analyzed notes. In FIG. 16 the results for single notes are illustrated. The different rows represent the data used for training of the neural network while the table columns correspond to the query data set. Although the note ranges for training and testing are identical for the shown results this does not mean that notes outside trained ranges cannot be found.

If both training and test data are identical, recognition rates of 100 percent can be achieved, i.e. the feature hold good training properties and the information is separable.

As expected, performing tests with different data sets for training and query (non-diagonal elements of rows 1-3), the recognition rates decrease because only one set of training data is not sufficient for generalizing the characteristic properties of the signals.

The results improve if two datasets are used for training purposes. Obviously better generalization by the network takes place analyzing the fed in features. Best recognition performance is obtained for bassoon inputs which seems plausible due to the small amount of overlap between the frequency ranges of the bassoon and the other two instruments.

The inventive method of analyzing a sound signal can be implemented in hardware in the form of a state machine or in software using a programmable processor. An inventive method, therefore, can be implemented on a computer readable medium on which the steps of the inventive method is stored in form of a code, which code results in an execution of the inventive method when the code is processed on a processor. The present invention is, therefore, also related to a computer program which results in the inventive method, when the program runs on a computer.

The invention claimed is:

1. A hardware apparatus for analyzing a sound signal, comprising:

an ear model for deriving, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and a pitch analyzer for analyzing the inner hair cell cleft contents map to obtain a pitch line over time, the pitch line indicating a pitch of the sound signal for respective time instants, wherein the pitch line varies in time over higher frequencies and lower frequencies as determined by the pitch analyzer;

wherein the pitch analyzer further comprises a vibration period detector, the vibration period detector being operative for calculating a summary auto correlation function for each time period of a number of adjacent time periods using the estimates for the transmitter concentrations of the number of inner hair cells;

wherein the vibration period detector is further operative, for each inner hair cell, to derive a time distance value T describing a time distance between two adjacent maxima in one estimate of the transmitter concentrations, and to enter a resulting time distance value T or a frequency value F derived from the time distance value T into a summary auto correlation function histogram, and wherein the ear model and the pitch analyzer are implemented using hardware or using a non-transitory computer readable medium storing computer instructions executable by a processor.

2. The hardware apparatus in accordance with claim 1, further comprising a rhythm analyzer for analyzing estimates for selected inner hair cells, the inner hair cells being selected in accordance with the pitch line, so that segmentation instants are obtained, wherein a segmentation instant indicates an end of a preceding note or a start of a succeeding note.

3. The hardware apparatus in accordance with claim 1, in which the ear model further comprises:

a mechanical ear model for modeling an auditory mechanical sound processing up to the inner ear to obtain estimates for representations of mechanical vibrations of a basilar membrane and lymphatic fluids; and an inner hair cell model for transforming the estimates for representations of mechanical vibrations into the estimates for the transmitter concentrations at the inner hair cells.

4. The hardware apparatus in accordance with claim 1, in which the ear model is operative to calculate a transmitter concentration for at least 100 inner hair cells, wherein each inner hair cell is associated with a specified area of a modeled basilar membrane, and wherein each inner hair cell has associated therewith a different specified area of the modeled basilar membrane.

5. The hardware apparatus in accordance with claim 1, in which the pitch analyzer is operative to retrieve a maximum value from each histogram of the time sequence of histograms, the maximum value representing a pitch in the time period so that pitch line points are obtained.

6. The hardware apparatus in accordance with claim 5, in which the pitch analyzer is further operative to build pitch line subtrajectories by combining pitch line points being close in time with respect to a time threshold and being close in frequency with respect to a frequency threshold.

7. The hardware apparatus in accordance with claim 6, in which the pitch line analyzer is further operative to fuse pitch line subtrajectories with a minimum length and to discard any subtrajectories not fulfilling a criterion related to a minimum length and amplitude.

8. The hardware apparatus in accordance with claim 1, further comprising a timbre recognition module, the timbre recognition module being operative for:

constructing a feature vector;

feeding the feature vector into a pattern recognition device; and obtaining a result indicating a probability that at least a portion of the sound signal has been produced by a sound source from a number of different specified sound sources.

9. The hardware apparatus of claim 1, wherein the pitch line over time is used for one or more members of the group comprising: performing a transcription, performing a sound source recognition, performing a music recognition, performing a query by humming process, displaying the pitch line over time, extracting auditory streams, identifying performing singers, and performing an instrument recognition.

10. A method of analyzing a sound signal, comprising:

deriving via at least one processor or hardware, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and analyzing via the at least one processor or hardware, the inner hair cell cleft contents map to obtain a pitch line over time, a pitch line indicating a pitch of the sound signal for respective time instants, wherein the pitch line varies in time over higher frequencies and lower frequencies as determined by analyzing the inner hair cell cleft contents map; and calculating via the at least one processor or hardware, a summary auto correlation function for each time period of a number of adjacent time periods using the estimates for the transmitter concentrations of the number of inner hair cells, wherein, for each inner hair cell, at least one time distance value T describing a time distance between two adjacent maxima in one estimate of the transmitter concentration is calculated, and wherein a resulting time distance value T or a frequency value F derived from the time distance value T is entered into a summary auto correlation function histogram.

11. The method of claim 10, wherein the pitch line over time is used for one or more members of the group comprising: performing a transcription, performing a sound source recognition, performing a music recognition, performing a query by humming process, displaying the pitch line over time, extracting auditory streams, identifying performing singers, and performing an instrument recognition.

12. A hardware apparatus for analyzing a sound signal, comprising:

an ear model for deriving, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and a pitch analyzer for analyzing the inner hair cell cleft contents map to obtain a pitch line over time, the pitch line indicating a pitch of the sound signal for respective time instants, wherein the pitch line varies in time over higher frequencies and lower frequencies as determined by the pitch analyzer;

a rhythm analyzer for analyzing estimates of the time-varying concentration of the transmitter substance for selected inner hair cells, the inner hair cells being selected in accordance with the pitch line obtained by the pitch analyzer, so that segmentation instants are obtained, wherein a segmentation instant indicates an end of a preceding note or a start of a succeeding note;

wherein the rhythm analyzer is configured to select an inner hair cell which vibrates with a pitch frequency or a partial frequency; and wherein the ear model, the pitch analyzer and the rhythm analyzer are implemented using hardware or using a non-transitory computer readable medium storing computer instructions executable by a processor.

13. The hardware apparatus in accordance with claim 12, in which the rhythm analyzer comprises a searcher for searching a dominant estimate for a transmitter concentration in a specified time period and comprising a dominant frequency determined by the pitch line so that, for adjacent time periods, corresponding dominant estimates for different inner hair cells are obtained, wherein the searcher is operative to acknowledge a dominant estimate, when the dominant estimate is above a threshold.

14. The hardware apparatus in accordance with claim 13, in which the threshold is an amplitude of an estimate comprising the second largest amplitude so that the dominant estimate comprises the largest amplitude in a specified time period.

15. The hardware apparatus in accordance with claim 12, in which the rhythm analyzer is operative to build an onset map by calculating an onset value for a dominant estimate for a specified time period, the onset map including a sequence of onset values.

16. The hardware apparatus in accordance with claim 15, in which the rhythm analyzer is operative to calculate an onset value such that an onset value is higher, when an onset comprises a stronger onset rise, compared to another onset comprising a weaker onset rise.

17. The hardware apparatus in accordance with claim 15, in which the rhythm analyzer is operative to calculate an onset value such that the onset value is higher, when a starting level before an onset is lower compared to another onset comprising a higher starting level.

18. The hardware apparatus in accordance with claim 12, in which the rhythm analyzer is operative to use an estimate for an inner hair cell representing a fundamental vibration or using an estimate for an inner hair cell representing at least one higher partial vibration.

19. The hardware apparatus in accordance with claim 12, in which the rhythm analyzer is operative to build an onset histogram by combining onset values of estimates for an inner hair cell representing a fundamental vibration, and onset values of an estimate for an inner hair cell representing at least one higher partial vibration, which comprises a time distance smaller than a specified time distance threshold.

20. The hardware apparatus in accordance with claim 19, in which the rhythm analyzer is operative to extract maxima from the onset histogram, wherein a time value associated with a maximum indicates a segmentation instant.

21. The hardware apparatus in accordance with claim 12, further comprising a transcription module, the transcription module being operative for using the pitch line segmented at segmentation instants to output a note description or a MIDI description.

22. The hardware apparatus according to claim 12, wherein the rhythm analyzer is configured to make use of certain transmitter concentration envelopes identified by the pitch line to perform segmentation of the pitch line.

23. A method of analyzing a sound signal, comprising:

deriving via at least one processor or hardware, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and analyzing via the at least one processor or hardware, the inner hair cell cleft contents map to obtain a pitch line over time, a pitch line indicating a pitch of the sound signal for respective time instants, wherein the pitch line varies in time over higher frequencies and lower frequencies as determined by analyzing the inner hair cells cleft contents map;

selecting via the at least one processor or hardware, inner hair cells in accordance with the pitch line obtained on a basis of an analysis of the inner hair cells cleft contents map, wherein an inner hair cell is selected which vibrates with a pitch frequency or in partial frequency; and analyzing via the at least one processor or hardware, estimates of the time-varying concentration of the transmitter substance for the selected inner hair cells, so that segmentation instants are obtained, wherein a segmentation instant indicates an end of a preceding note or a start of a succeeding note.

24. A hardware apparatus for analyzing a sound signal, comprising:

an ear model for deriving, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and a pitch analyzer for analyzing the inner hair cell cleft contents map to obtain a pitch line over time, the pitch line indicating a pitch of the sound signal for respective time instants, wherein the pitch line varies in time over higher frequencies and lower frequencies as determined by the pitch analyzer;

a timbre recognition module, the timbre module being operative for:

constructing a feature vector;

feeding the feature vector into a pattern recognition device; and obtaining a result indicating a probability that at least a portion of the sound signal has been produced by a sound source from a number of different specified sound sources;

wherein the timbre recognition module is configured to construct the feature vector such that the feature vector comprises feature values describing relationship between frequencies of higher order partial vibration and a frequency of fundamental vibration such that a deviation of partial frequencies from an ideal integer relationship of harmonics can be seen; and wherein the ear model, the pitch analyzer and the timbre recognition module are implemented using hardware or using a non-transitory computer readable medium storing computer instructions executable by a processor.

25. The hardware apparatus in accordance with claim 24, in which the pattern recognition device is a neural network.

26. The hardware apparatus in accordance with claim 24, in which the feature vector further comprises one or more selected members from a feature group including onset time of a fundamental vibration or a higher order partial vibration, a frequency of a fundamental vibration or a higher order partial vibration, an amplitude of a fundamental vibration or a higher order partial vibration, a number of an estimate for the transmitter concentration using the highest peak for the fundamental vibration or the higher order partial vibration, or a number of an estimate for the transmitter concentration being in resonance for a fundamental vibration or a higher order partial vibration.

27. The hardware apparatus according to claim 24, wherein the timbre recognition module is configured to construct the feature vector such that the feature vector comprises feature values describing differences between times at which cleft content envelopes of partials and a cleft content envelope of the fundamental reach maxima.

28. A method of analyzing a sound signal, comprising:

deriving via at least one processor or hardware, for a number of inner hair cells, an estimate for a time-varying concentration of a transmitter substance inside a cleft between an inner hair cell and an associated auditory nerve from the sound signal, so that an estimated inner hair cell cleft contents map over frequency and over time is obtained, wherein the inner hair cells comprising lower order inner hair cells indicating lower frequencies and higher order inner hair cells indicating higher frequencies; and analyzing via the at least one processor or hardware, the inner hair cell cleft contents map to obtain a pitch line over time, a pitch line indicating a pitch of the sound signal for respective time instants, wherein the pitch line varies in time over higher frequencies and lower frequencies as determined by analyzing the inner hair cell cleft contents map; and performing via the at least one processor or hardware, a timbre recognition, wherein performing a timbre recognition comprises:

constructing via the at least one processor or hardware, a feature vector, such that the feature vector comprises feature values describing relations of frequencies of higher partials and the fundamental, and performing via the at least one processor or hardware, a pattern recognition on a basis of the feature vector, to obtain a result indicating a probability that at least a portion of the sound signal has been produced by a sound source from a number of different specified sound sources, such that a deviation of partial frequencies from an ideal integer relationship of harmonics can be seen.

* * * * *